(12) United States Patent
Nicoletti et al.

(10) Patent No.: US 10,588,232 B2
(45) Date of Patent: Mar. 10, 2020

(54) ELECTRONIC COMPONENT WITH A METAL RESISTOR SUSPENDED IN A CLOSED CAVITY

(71) Applicant: COMMISSARIAT A L'ENERGIE ATOMIQUE ET AUX ENERGIES ALTERNATIVES, Paris (FR)

(72) Inventors: Sergio Nicoletti, Sinard (FR); Mickaël Brun, Eybens (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/076,855

(22) PCT Filed: Feb. 7, 2017

(86) PCT No.: PCT/FR2017/050278
§ 371 (c)(1),
(2) Date: Aug. 9, 2018

(87) PCT Pub. No.: WO2017/137694
PCT Pub. Date: Aug. 17, 2017

(65) Prior Publication Data
US 2019/0045648 A1 Feb. 7, 2019

(30) Foreign Application Priority Data
Feb. 12, 2016 (FR) .................................... 16 51129

(51) Int. Cl.
*H05K 5/06* (2006.01)
*H05K 5/00* (2006.01)
(Continued)

(52) U.S. Cl.
CPC .............. *H05K 5/069* (2013.01); *G01J 3/108* (2013.01); *G01N 21/3504* (2013.01); *H05K 5/0004* (2013.01); *H05K 5/0247* (2013.01)

(58) Field of Classification Search
CPC .... H05K 5/069; H05K 5/0004; H05K 5/0247; G01J 3/108; G01N 21/3504
(Continued)

(56) References Cited

U.S. PATENT DOCUMENTS 5,668,033 A    9/1997  Ohara et al.
5,895,233 A *  4/1999  Higashi .................... G01J 5/04
                                              257/E27.008

(Continued)

FOREIGN PATENT DOCUMENTS

WO    WO 98/43281       10/1998
WO    WO 2006/031125 A1  3/2006

OTHER PUBLICATIONS

International Search Report dated Jun. 22, 2017 in PCT/FR2017/050278 filed Feb. 7, 2017.
(Continued)

*Primary Examiner* — Taeho Jo
(74) *Attorney, Agent, or Firm* — Oblon, McClelland, Maier & Neustadt, L.L.P.

(57) ABSTRACT

The invention relates to an electronic component for producing infrared radiation. Said component includes a first element and a second element arranged so as to form a closed vacuum cavity in which at least one resistive element of said electronic component is suspended, the at least one resistive element including metal. Said first and second elements are connected by eutectic solder so as to sealingly close the cavity. Said electronic component comprises connection terminals located outside the closed cavity and connected electrically to the suspended resistive element.

16 Claims, 7 Drawing Sheets

(51) Int. Cl.
*H05K 5/02* (2006.01)
*G01N 21/3504* (2014.01)
*G01J 3/10* (2006.01)

(58) Field of Classification Search
USPC .................................................. 250/339.07
See application file for complete search history.

(56) References Cited

U.S. PATENT DOCUMENTS

| | | | |
|---|---|---|---|
| 5,955,839 A | 9/1999 | Jaffe et al. | |
| 6,297,511 B1* | 10/2001 | Syllaios | F41J 2/02 250/495.1 |
| 6,392,232 B1* | 5/2002 | Gooch | G01J 5/20 250/332 |
| 8,659,167 B1 | 2/2014 | Bowles et al. | |
| 8,709,868 B2 | 4/2014 | Bowles et al. | |
| 8,859,303 B2 | 10/2014 | Udrea et al. | |
| 2001/0044197 A1* | 11/2001 | Heinen | H01L 21/67138 438/612 |
| 2002/0000649 A1* | 1/2002 | Tilmans | B81B 7/0077 257/678 |
| 2003/0041649 A1* | 3/2003 | George | G01J 3/10 73/24.02 |
| 2003/0209534 A1* | 11/2003 | Ferguson | C04B 35/117 219/548 |
| 2005/0189622 A1* | 9/2005 | Humpston | B81B 7/0077 257/659 |
| 2007/0105341 A1* | 5/2007 | Sosnowchik | B23K 1/0016 438/455 |
| 2007/0259470 A1* | 11/2007 | Quenzer | B81B 7/0077 438/50 |
| 2008/0141759 A1* | 6/2008 | Reinert | G01M 3/186 73/40 |
| 2008/0272389 A1 | 11/2008 | Rogne et al. | |
| 2009/0098710 A1* | 4/2009 | Yamazaki | H01L 21/268 438/458 |
| 2009/0140149 A1* | 6/2009 | Tinnes | G01J 5/04 250/352 |
| 2010/0025845 A1* | 2/2010 | Merz | B81B 7/0038 257/723 |
| 2010/0099268 A1* | 4/2010 | Timans | H01L 21/67115 438/761 |
| 2010/0151676 A1* | 6/2010 | Ritchie | C23C 16/34 438/660 |
| 2010/0213500 A1* | 8/2010 | Rogne | G01J 3/108 257/99 |
| 2011/0057107 A1* | 3/2011 | Agnese | G01J 5/08 250/338.3 |
| 2012/0097415 A1* | 4/2012 | Reinert | H01L 27/14618 174/50 |
| 2012/0132522 A1* | 5/2012 | Foster | B81C 1/00285 204/298.11 |
| 2012/0228733 A1* | 9/2012 | Garcia-Blanco | B81B 7/0038 257/467 |
| 2012/0267532 A1* | 10/2012 | Udrea | H05B 3/267 250/338.5 |
| 2013/0199730 A1* | 8/2013 | Gudeman | H01L 21/67092 156/379.6 |
| 2014/0186999 A1* | 7/2014 | Schweikert | H01L 21/67109 438/106 |
| 2014/0291704 A1* | 10/2014 | Ali | H01L 33/34 257/88 |
| 2015/0158720 A1* | 6/2015 | Lim | B81C 1/00285 257/415 |
| 2015/0204827 A1* | 7/2015 | Duraffourg | G01N 30/7206 250/288 |
| 2015/0221865 A1* | 8/2015 | Tada | H01L 27/101 257/4 |
| 2015/0316472 A1* | 11/2015 | Yon | G01J 5/0025 356/437 |
| 2016/0167953 A1* | 6/2016 | Gogoi | H01L 27/14 257/414 |
| 2016/0308084 A1* | 10/2016 | Bieselt | G01J 3/00 |
| 2016/0324443 A1* | 11/2016 | Rowland | A61B 5/076 |
| 2016/0344159 A1* | 11/2016 | Sherrer | G02B 6/4201 |
| 2016/0349201 A1* | 12/2016 | Graunke | G01N 27/123 |
| 2017/0191868 A1* | 7/2017 | Kurth | H01L 27/14623 |
| 2017/0288125 A1* | 10/2017 | Glacer | H01L 41/0805 |
| 2017/0355596 A1* | 12/2017 | Gogoi | H01L 27/14 |
| 2017/0363589 A1* | 12/2017 | Kumar | G01N 25/18 |

OTHER PUBLICATIONS

"Eutectic bonding", Wikipedia, May 24, 2015, 12 total pages, XP055311433.

Barritault, P. et al., "Mid-IR source based on a free-standing microhotplate for autonomous $CO_2$ sensing in indoor applications", Sensors and Actuators A: Physical, vol. 172 (2011), pp. 379-385, XP028336715.

Elmi, I. et al., "Development of Ultra Low Power Consumption Hotplates for Gas Sensing Applications", IEEE Sensors 2006, Oct. 2006, pp. 243-246.

Cozzani, E. et al., "Material Properties Measurement and Numerical Simulation for Characterization of Ultra-Low-Power Consumption Hotplates", Transducers & Eurosensors, 3EB1.P, 2007, pp. 1661-1664.

Farrens, S. et al., "Precision Wafer to Wafer Packaging Using Eutectic Metal Bonding", pp. 6-11 (3 sheets).

* cited by examiner

ELECTRONIC COMPONENT WITH A METAL RESISTOR SUSPENDED IN A CLOSED CAVITY

FIELD OF THE INVENTION

The present invention relates to the field of the generation of infrared radiation, in particular in the field of gas detection.

PRIOR ART

In the field of the detection of gases, a known solution is to use a non-dispersive infrared sensor. Such a non-dispersive infrared sensor is also known by the term NDIR (acronym for NonDispersive InfraRed).

Such an infrared sensor comprises an infrared source—also called electronic component—for generating infrared radiation in the following part of the description. In the literature, sources based on a filament deposited on silicon or suspended have already been used. The document "Sensors and Actuators A: Physical" in the article whose title is "Mid-IR source based on a free-standing microhotplate for autonomous $CO_2$ sensing in indoor applications" by P. Barritault et al. published in "Sensors and Actuators A 172 (2011) 379-385" notably describes a way of forming a source by using a metal resistive element suspended by arms above an open cavity. The source described in this document allows infrared radiation to be emitted while limiting the consumption in terms of power of the source in order to reach a suitable working temperature.

A source such as described in the document hereinabove is suitable when sufficient optical power is available. Today, there does however exist a need to further reduce the electrical power needed for the operation of the infrared source.

The document US2003/0041649, on the other hand, describes a device equipped with a cavity formed by the assembly of three independent elements that are bonded together in pairs, notably by eutectic soldering. The large-scale production of such a device is difficult owing to the parts to be manipulated, which can pose a problem by furthermore increasing the risks of leaks between the interior of the cavity and the exterior of the cavity.

Furthermore, another requirement is to conserve a source of limited size and that can be produced with a suitable throughput and at a suitable cost.

SUBJECT OF THE INVENTION

The aim of the invention is to provide a solution to at least a part of the aforementioned problems.

This goal may be achieved by virtue of an electronic component for generating infrared radiation, said electronic component comprising a first element and a second element arranged in such a manner as to form an enclosed cavity under vacuum within which at least one resistive element of the said electronic component is suspended, said at least one resistive element comprising metal, the said first and second elements being joined by eutectic soldering allowing the cavity to be sealed in a leak-tight manner, said electronic component comprising connection terminals situated outside of the enclosed cavity and electrically connected to the suspended resistive element.

Notably, the eutectic soldering is formed with silicon and gold, or Cu and Sn, or Au and Sn, or Au and Ge, or Al and Ge, or Au and In.

Preferably, the enclosed cavity has an internal pressure of less than $10^{-2}$ mbar, and notably comprised between $10^{-3}$ mbar and $10^{-2}$ mbar.

Notably, a residual gas trap is situated within the enclosed cavity.

The resistive element may be suspended by suspension arms belonging to the first element.

According to a first case, the first element comprises the connection terminals.

According to a second case, the second element comprises the connection terminals, the first element comprises connection pads electrically connected to the resistive element, the connection terminals each being in electrical contact with at least one of the connection pads.

According to one embodiment, the resistive element comprises at least one structured part of a stack comprising the following successive layers: a first barrier layer against the diffusion of a metal layer, the metal layer notably being platinum, a second barrier layer against the diffusion of the metal layer, preferably the first and second barrier layers are of titanium nitride.

Furthermore, said stack can form a part of the suspension arms of the resistive element and extends in the direction of the connection terminals.

Preferably, the closure of the enclosed cavity is provided by a single ribbon of eutectic soldering.

In particular, the enclosed cavity is bounded, at least in part, by a hollow formed in the first element, said hollow comprising a bottom oriented towards the resistive element, said hollow being bounded by a continuous surface of the same material.

The invention also relates to a method for fabricating a plurality of electronic components such as described, in this case, the method comprises the following steps: a step for supplying a first plate comprising a base, preferably made of silicon, on which a plurality of first hollows is formed, the said first plate comprising suspended resistive elements comprising metal, and each first hollow is associated with at least one of the suspended resistive elements and disposed facing the bottom of the said first hollow; a step for supplying a second plate, preferably formed entirely or in part of silicon, comprising second hollows intended to cooperate with the said first hollows for the purpose of forming the enclosed cavities of the electronic components; a step for assembling the first and second plates comprising a step for eutectic soldering implemented in a chamber under vacuum which results in: formation of the enclosed cavities, under vacuum and leak tight, and localization of connection terminals of the resistive elements in hollow spaces bounded by the first and second plates and formed outside of the enclosed cavities; a step for removal of material in the hollow spaces in order to make the connection terminals accessible.

Furthermore, the method may also comprise a step for separation of the electronic components by removal of material.

Notably, the step for eutectic soldering uses gold and silicon, or Cu and Sn, or Au and Sn, or Au and Ge, or Al and Ge, or Au and In, brought into contact.

According to one embodiment, the method comprises, prior to the assembly step, for each first hollow, a step for formation of a closed track of a first material, preferably gold, arranged at the periphery of the said first hollow, and the second plate comprises bearing faces made of a second material, preferably silicon, each disposed in contact against the corresponding track during the assembly step, the eutectic soldering step comprising a step for pushing the first and second plates towards each other while applying a suitable temperature in order to form the eutectic soldering from first and second materials.

According to one case, the first plate comprises the connection terminals, and the step for removal of material is implemented by removal of material belonging to the second plate.

Notably, according to this case, the step for removal of material may be implemented by one of the techniques chosen from amongst: sawing, polishing, etching.

Furthermore, according to this case, the separation step may comprise the removal of material belonging to the first plate, notably by sawing.

According to another case, the method is such that: the connection terminals are carried by the second plate; the first plate comprises connection pads each electrically connected to at least one resistive element, and third hollows intended to form the hollow spaces; the result of the assembly step is an electrical contact being made between the connection pads with the corresponding connection terminals and the formation of the hollow spaces comprising the connection terminals.

Notably, according to this other case, the step for removal of material is implemented by removal of material belonging to the first plate in the hollow spaces.

Furthermore, according to this other case, the step for removal of material from the first plate may be implemented by one of the techniques chosen from amongst: sawing, polishing, etching.

Lastly, according to this other case, the separation step comprises the removal of material belonging to the second plate, notably by sawing.

The invention also relates to a use of an electronic component such as described as a source of infrared radiation for gas detection.

The invention also relates to a gas detector comprising an electronic component such as described and a sensor capable of measure infrared radiation coming from the electronic component.

BRIEF DESCRIPTION OF THE FIGURES

The invention will be better understood upon reading the description that follows, presented solely by way of non-limiting example and with reference to the drawings in which:

FIGS. 20 and 21, on the other hand, show a cross section including the suspension arms.

In these figures, the same references are used to identify the same elements.

Furthermore, the elements shown in the figures are not to scale.

DESCRIPTION OF PARTICULAR EMBODIMENTS

The electronic component described hereinafter differs from the prior art in that the resistive element is encapsulated under vacuum and in a leak-tight manner within an enclosed cavity. Operating under vacuum allows the thermal conduction of the infrared radiation emitted by the resistive element with gases in contact with said resistive element to be avoided notably allowing the electrical power consumption to be limited. This solution leads to a problem of closing of the cavity and of leak-tight sealing of the latter. In order to obtain the enclosed cavity, we propose here to use a solder joint between two elements (notably a support and a lid) that does not degrade the electronic component, notably when the latter comprises electrical contacts (terminals and/or connection pads) or else a gas trap of the Getter type. It is for this purpose that the solution provided for the closing of the cavity includes a low-temperature solder process of the eutectic soldering type, notably between gold and silicon. Aside from the resolution of the degradation issue, a eutectic soldering provides a solution in synergy with the problem of sealing of the cavity and of large-scale production with suitable throughputs and costs. In the present application, the electronic component could be used by heating the resistive element to a temperature above 200° C. in order to emit infrared radiation in the range 3 μm to 5 μm.

In the present description, when the term "around" is used in combination with a value, this is understood to mean the exact value or more or less 10% of the given value.

Figure 1:
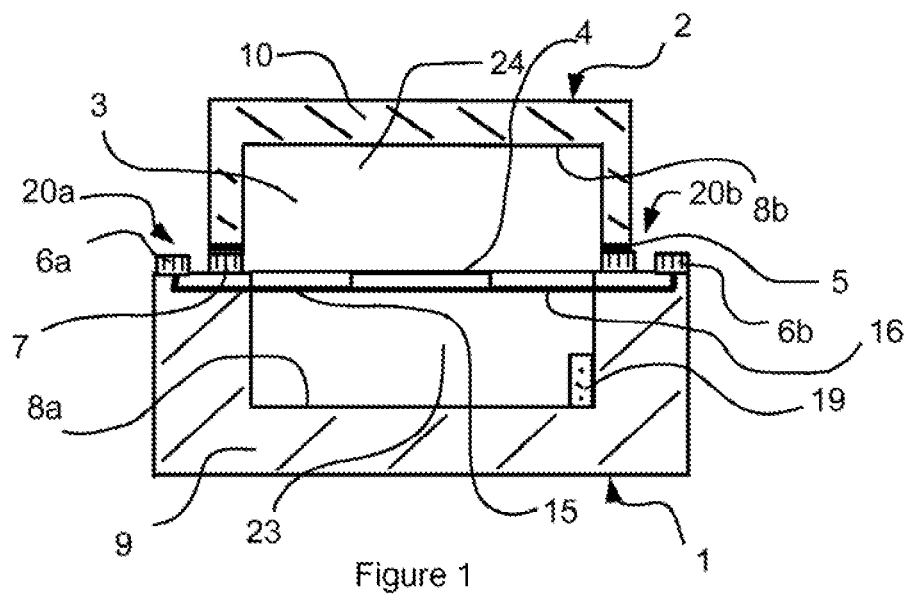
FIG. 1 illustrates an electronic component according to one embodiment of the invention.
Figure 2:
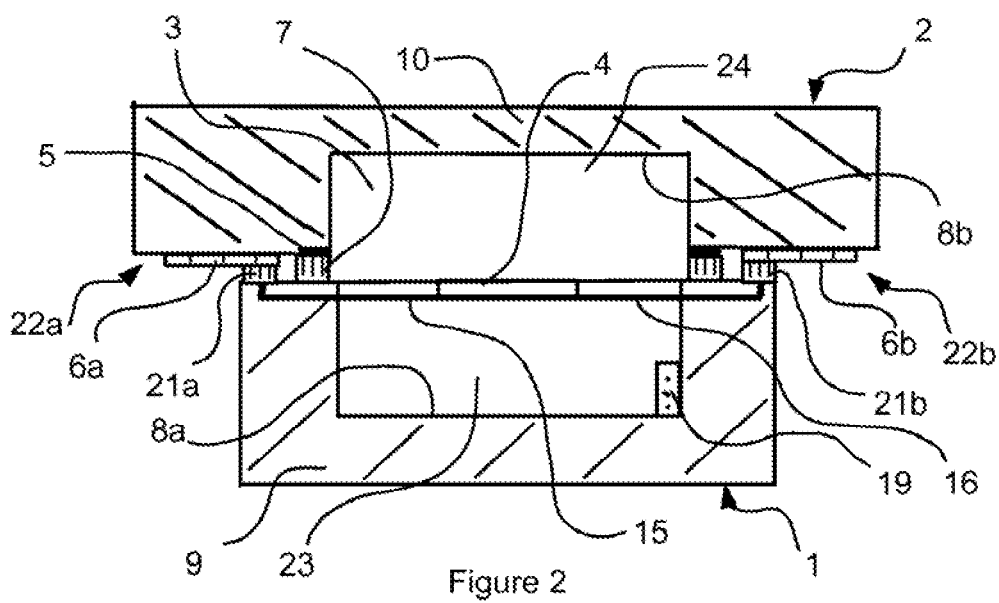
FIG. 2 illustrates an electronic component according to another embodiment of the invention.

FIGS. 1 and 2 illustrate a schematic cross-sectional view of an electronic component according to two different embodiments of the invention. In general, the electronic component for generating infrared radiation comprises a first element 1 and a second element 2 arranged in such a manner as to form an enclosed cavity 3 under vacuum within which at least one resistive element 4 of the said electronic component is suspended. It will then be understood that there may be several resistive elements within the same enclosed cavity 3, everything that is applicable, in the present description, for one resistive element 4 per cavity 3 may therefore be implemented for several resistive elements 4 per cavity 3 or at least one resistive element 4. The resistive element is an electrically resistive element able to be heated and to emit infrared radiation. The resistive element 4 comprises metal, in particular platinum. The phrase "resistive element that comprises metal" is understood to mean that the resistive element comprises at least one metal layer which is structured in order to form an electrical resistor. The operating temperature of the resistive element 4 may be a maximum of 650° C., but any temperature between room temperature and the maximum temperature may be allowed. Having said that, below 300° C.-350° C. the optical power is less. The said first and second elements 1, 2 are joined by eutectic soldering 5 allowing the cavity 3 to be closed in a leak-tight manner. Furthermore, the electronic component comprises connection terminals 6a, 6b situated outside of the cavity 3 and electrically connected to the suspended resistive element 4.

The term "eutectic soldering" is understood to mean the presence of a eutectic alloy, notably formed by gold and silicon, and in particular obtained by thermo-compression.

The eutectic soldering may also be obtained/formed with the following materials Cu and Sn, or Au and Sn, Au and Ge, Al and Ge, or Au and In. In other words, the eutectic soldering 5 (also known in the field as eutectic bonding) is the result of a eutectic soldering step which results in the formation of an alloy starting from a first material and from a second material different from the first material, in particular from gold and silicon. The materials Au and Si, or Au and Ge, or Al and Ge are preferred. For this purpose, the first element 1 may comprise a closed track made of a first material (notably gold) 7 and the second element 2 may be made from, or comprise, the second material (notably silicon), the eutectic soldering 5 (for example the alloy SiAu) then being formed at the interface between the second element 2 and the first element 1. Depending on the case, the second element 2 may also comprise an additional track in such a manner that the track 7 and the additional track are joined via a eutectic alloy coming from the material of the track 7 and of the additional track. By studying the electronic component, notably at the interface between the first and second elements 1, 2, it is possible to discover whether the bonding between the latter has been well formed by eutectic soldering or otherwise since the solder bond then possesses particular and identifiable characteristics; it is for example possible to see whether the silicon has correctly migrated into the gold. The advantage of such a eutectic soldering is that it can be formed at low temperature. "Low temperature" is understood preferably to mean a temperature comprised between 350° C. and 400° C., and preferably equal to 350° C. which notably avoids the fusion of the layer or layers notably forming the connection terminals 6a, 6b and potentially the gas trap that will be described hereinafter. In general, in the following part of the description, reference is made to the gold-silicon alloy as a eutectic soldering, but of course the alloys of the materials specified hereinabove (Au and In, or Cu and Sn, or Au and Sn, Au and Ge, Al and Ge) may be used as a substitution for SiAu. Those skilled in the art will therefore be able to adapt the structure of the electronic component and the method for closing the cavity by soldering for the purpose of forming a eutectic soldering according to the various possibilities of materials.

The connection terminals 6a, 6b (naturally electrically conducting) allow the resistive element 4 to be electrically powered from the outside of the enclosed cavity 3 in such a manner that temperature of the latter rises and causes the emission of the desired infrared radiation. These connection terminals 6a, 6b, and, where relevant, the connection pads described hereinafter preferably comprise gold or aluminium.

The electronic component is notably configured in such a manner that the infrared radiation emitted by the resistive element 4 when the latter is electrically powered is radiated outside of the cavity 3. For this purpose, the enclosed cavity 3 may be bounded, at least in part, by walls 8a, 8b that are transparent in the infrared, preferably made of silicon, notably of single-crystal or polycrystalline silicon, or of any other material that is transparent in the infrared. "Transparent in the infrared" is understood to mean that the materials used can allow a transmissivity in the infrared of around 50% to 60%, notably when it is not used as antireflective coating. "Other material transparent in the infrared" is understand to mean for example germanium, AlGaS, GaS, or InP. In other words, in order to allow the passage of the infrared radiation emitted by the resistive element 4 from the interior of the enclosed cavity 3 to the exterior of the latter, the first and second elements 1, 2 respectively comprise parts 9, 10 made of silicon—or of one or more of the other transparent materials previously specified. In the case of silicon used for its transparency to infrared, single-crystal or polycrystalline silicon is used. More particularly, the first element 1 comprises a substrate 9 made of silicon (notably single-crystal or polycrystalline) and the second element 2 comprises a lid 10 made of silicon (notably single-crystal or polycrystalline).

In order to allow the presence of the connection terminals 6a, 6b outside of the enclosed cavity 3, the first element 1 may comprise various stacked layers (in particular starting from the substrate 9) allowing this function; notably, at least one metal layer may be used disposed between electrically-insulating layers.

In general, the first element 1 may be obtained in the same way as—and hence comprising the characteristics of—the electronic component described in "Sensors and Actuators A: Physical" in the article whose title is "Mid-IR source based on a free-standing microhotplate for autonomous $CO_2$ sensing in indoor applications" by P. Barritault et al. published in "Sensors and Actuators A 172 (2011) 379-385". It is on this first element 1 that a closed track 7 can then be added, in particular made of gold, intended to form a eutectic alloy (notably of gold/silicon) by virtue of the use of the second element 2 (notably silicon).

Figure 3:
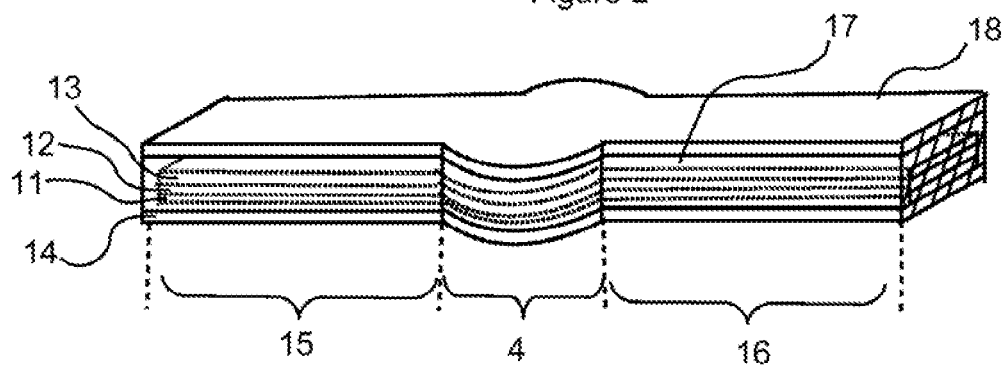
FIG. 3 illustrates schematically a part of the electronic component which is suspended within the cavity.

More precisely, the resistive element 4 may comprise, as illustrated in FIG. 3, at least one structured part of a stack of layers comprising the following successive layers: a layer of titanium nitride 11 (with a thickness preferably comprised between 10 nm and 100 nm), a layer of platinum 12 (with a thickness preferably comprised between 10 nm and 100 nm), another layer of titanium nitride 13 (with a thickness preferably comprised between 10 nm and 100 nm). More generally, the layer of platinum 12 is a metal layer forming the electrical resistance of the resistive element, and the layers of titanium nitride 11, 13 more generally form first and second barrier layers against the diffusion of the metal layer 12 (in particular of platinum).

This stack of layers may extend from a layer 14 for relaxation of the stresses, in particular of $Si_3N_4$ and notably with a thickness preferably comprised between 100 nm and 500 nm, forming, on the one hand, a support base for the resistive element 4 and, on the other hand, a support base 15, 16 (FIGS. 1 and 2) for the suspension arms of the resistive element 4. These suspension arms 15, 16 are preferably anchored to the silicon substrate 9 of the first element 1 described hereinbefore, in particular by a contact of the relaxation layer 14 with said substrate 9. In other words, the resistive element 4 may be suspended by suspension arms 15, 16 belonging to the first element 1. The suspension arm 15, 16 are preferably anchored to the support, or substrate 9, by bonding atoms from a layer deposited on the support or substrate 9.

The advantage of the aforementioned use of platinum to form a part of the resistive element 4 is that this material is a good candidate for forming a heating resistive element since it is mechanically, chemically and electrically stable at high temperature. The layers of titanium nitride 11, 13 allow:
   a good adhesion layer to be formed on layers containing silicon such as $Si_3N_4$,
   a platinum diffusion barrier to be formed for limiting the thermal drift when the temperature of the resistive element rises,
   this is a good emitter of radiation, hence compatible with the emission of photons notably in the infrared spectral band: it therefore allows the emission to be maximized.

As illustrated in FIG. 3, the stack of layers described hereinbefore forms at least one part of the suspension arms 15, 16 of the resistive element 4 and extends in the direction of the connection terminals 6a, 6b (notably on either side of the resistive element 4). In other words, parts of this stack, distinct from the part associated with the resistive element 4, therefore allow electrical connections to be formed between the resistive element 4 and the connection terminals 6a, 6b. It will be understood that FIG. 3 shows schematically the resistive element 4 and the suspension arms 15, 16 disposed within the cavity 3. These suspension arms also furthermore extend outside of the enclosed cavity so as to be anchored onto the substrate 9 and to form contact formation areas which will be able to be electrically connected to the connection terminals 6a, 6b or to connection pads 21a, 21b as will be see hereinbelow. Although not shown, it is noted that the structure may include additional arms without electrical connections but only present to give a mechanical stability to the resistive element 4. These additional arms may, for example, connect the resistive element to the wall of the cavity without altering the operation of the resistive element 4.

The stack of layers could furthermore be covered with a layer of $SiO_2$, notably with a thickness comprised between 50 nm and 500 nm, serving as a passivation layer 17 itself covered by a layer of $Si_3N_4$ 18, notably with a thickness comprised between 100 nm and 500 nm, allowing another layer for relaxation of the stresses to be formed. In particular, the passivation layer 17 covers the sidewalls of the layers 11, 12 and 13 and also the top of these layers (in other words the top of the stack), except for a contact formation area for the connection terminals. It is for this reason that the layers 11, 12, 13 in FIG. 3 are shown as dashed lines since "buried" in the passivation layer.

The track 7, preferably made of gold, at least one part of which has been used to form the aforementioned eutectic, preferably rests on a layer of $Si_3N_4$ which surrounds the enclosed cavity 3.

In general, the enclosed cavity 3 has an internal pressure of less than $10^{-2}$ mbar (or 1 Pascal) and notably comprised between $10^{-3}$ mbar (or 0.1 Pascal) and $10^{-2}$ mbar. It will therefore be understood that the leak-tight sealing of the cavity 3 is such that this pressure is maintained in the cavity 3 over time. Notably, this internal pressure defines the vacuum of the cavity 3.

The result of the fabrication of such an electronic component is that, over time, molecules imprisoned in the materials at the walls of the enclosed cavity 3 can diffuse into the enclosed cavity 3. The presence of such molecules within the enclosed cavity 3 is detrimental to the correct operation of the electronic component in the sense that they risk increasing the power consumed in order to reach the working temperature of the resistive element 4. In order to resolve this issue, the incorporation of a gas trap 19 (FIGS. 1 and 2) into the electronic component is provided. In other words, the electronic component comprises a residual gas trap 19 situated within the enclosed cavity 3. Such a gas trap 19 is also known in the field as a "Getter". The gas trap 19 allows the absorption of molecules so that the latter do not interfere with the rise in temperature of the resistive element 4 and allows the aforementioned pressure within the enclosed cavity 3 to be maintained. The gas trap is preferably placed away from the resistive element 4 and suspension arms 15, 16 carrying it. Another advantage of the use of a eutectic soldering 5, notably between gold and silicon, is that, in view of temperatures implemented in its formation, the latter allows the Getter present within the enclosed cavity 3 to be activated without it being degraded at the time when the cavity is sealed. Indeed, the gas trap may be degraded when it reaches temperatures greater than 400° C.: as a consequence, the use of a eutectic soldering is particularly compatible with such a gas trap. It will then be understood that those skilled in the art will be able to choose a gas trap adapted to the production of the electronic component. In particular, the gas trap chosen is of the type to be activated at the temperature of eutectic soldering but without degrading at this soldering temperature. For example, the gas trap may comprise a mixture of metals including titanium.

According to one particular example, the resistive element 4 has a diameter around 150 μm to 250 μm, and a maximum height comprised between 100 nm and 1000 nm and more particularly equal to 300 nm. The suspension arms 15, 16 carrying this resistive element 4 and connecting the resistive element 4 to the internal walls of the enclosed cavity have a lateral dimension comprised between 10 μm and 100 μm and notably equal to 40 μm, a maximum height comprised between 100 nm and 1000 nm and more particularly equal to 300 nm, and a length between the internal wall of the enclosed cavity 3 and the resistive element comprised between 300 μm and 1000 μm and notably equal to 350 μm.

The internal dimensions of the enclosed cavity 3 are notably chosen so as to avoid the resistive element 4 and/or the suspension arms 15, 16 of the resistive element 4 coming into contact against an internal face of the cavity 3 in the case of movement of the resistive element 4 within the cavity 3 notably caused by thermal expansions. Indeed, such a contact could deteriorate definitively the electronic component by the effect of sticking the resistive element 4 and/or suspension arms 15, 16 against the said internal face of the cavity 3. It is for this reason that, in a normal configuration of the resistive element 4 within the cavity 3, the latter is separated from the walls of the cavity 3 by a distance of at least 5 μm and notably comprised between 10 μm and 100 μm. In particular, by considering a plane of inclusion of the resistive element 4, two opposing internal faces of the cavity 3 are respectively included in first and second planes parallel to the said plane of inclusion. Here, the minimum separation distances of each of the two opposing internal faces with respect to the resistive element may be around 80 μm and notably comprised between 50 μm and 80 μm. In fact, the electronic component may be such that the first element 1 comprises a first hollow 23 and that the second element 2 comprises a second hollow 24 which, in cooperation with the first hollow 23, forms the enclosed cavity 3 (FIGS. 1 and 2). The first hollow 23 may comprise a depth comprised between 50 μm and 100 μm and notably equal to 80 μm. The depth of the first hollow 23 is notably such that it results from an anisotropic etching of the silicon substrate (in this case, the silicon substrate is single-crystal silicon) underneath the resistive element 4 during the fabrication of the first element 1. The second hollow 24 may comprise a depth comprised between 5 μm and 300 μm and notably equal to 80 μm. Furthermore, the first and second hollow 23, 24 may have lateral dimensions comprised between 300 μm and 1000 μm and notably equal to 350 μm. In general, the result of this is that the enclosed cavity 3 can have a volume comprised between $1 \times 10^{-6}$ cm$^3$ and $1 \times 10^{-4}$ cm$^3$ and notably equal to $2 \times 10^{-5}$ cm$^3$.

Thus, one hollow (for example the first hollow or the second hollow) may be a concave part, or a depression, arranged within the element concerned. The hollow comprises a bottom and an opening allowing the access to the volume of the hollow. A hollow then forms a recess in one component, here for example in the element concerned. The opening and the bottom of the hollow are connected by a sidewall of the hollow. A sidewall of the hollow may comprise one or more faces. A hollow is then effectively a blind hole, in other words the hollow is not a through-hole.

The enclosed cavity 3 may be bounded, at least in part, by a hollow 23 formed in the first element 1, said hollow 23 comprising a bottom oriented towards the resistive element 4, said hollow 23 being bounded by a continuous surface of the same material, for example silicon. The hollow 23 formed in the first element 1 is also called first hollow 23 in the sense that the cavity 3 may also be bounded, at least in part, by a second hollow 24 formed in the second element 2, said second hollow 24 comprising a bottom oriented towards the resistive element 4, and said second hollow 24 being bounded by a continuous surface of the same material, for example silicon. In particular, the first hollow 23 comprises a bottom and a sidewall formed by a continuous surface of the same material, for example silicon, and the second hollow 24 comprises a bottom and a sidewall formed by a continuous surface of the same material for example silicon.

It will then be understood that the first element 1 may comprise the first hollow 23 and that the resistive element 4 extends, at least in part, facing the bottom of the first hollow 23. Thus, the cooperation of the first hollow 23 of the first element 1 with the second element 2 then soldered by eutectic soldering to the first element 1 allows the enclosed cavity 3 to be formed. With respect to the embodiment in the document US2003/0041649, we propose here to use two elements having hollows and a single eutectic soldering in order to enclose the enclosed cavity 3. As a consequence of this, large-scale production is easier and the probabilities of leaks are limited owing to the use of a single eutectic soldering.

According to one embodiment, the first element 1 comprises a single-piece base, or substrate 9, the first hollow 23 is formed in this base, notably under the resistive element 4, a bottom of the first hollow 23 being oriented towards the resistive element 4. The second hollow 24 may be formed within the second element 2, notably in at least one part of the latter.

Preferably, it will be understood that, in the framework of the electronic component, the closing of the enclosed cavity 3 may be provided by a single ribbon of eutectic soldering for the purpose of limiting the possibilities of leaks between the interior of the cavity 3 and the exterior of the enclosed cavity 3.

In a first case illustrated in FIG. 1, it is the first element 1 which comprises the connection terminals 6a, 6b. As can be observed, the assembly of the first 30 element 1 with the second element 2 allows two portions 20a, 20b of the first element 1 to be conserved that are situated on the same face of the said first element 1 and which extend from an interface region between the first element 1 and the second element 2 in opposite directions on either side of the said second element 2. The connection terminals 6a, 6b extend from these portions 20a, 20b.

In a second case illustrated in FIG. 2, it is the second element 2 which comprises the connection terminals 6a, 6b. In this case, the first element 1 comprises connection pads 21a, 21b (naturally electrically conducting) disposed outside of the enclosed cavity 3 and electrically connected to the resistive element 4. Furthermore, each of the connection terminals 6a, 6b is in electrical contact with at least one of the connection pads 21a, 21b. As can be observed, the assembly of the first element 1 with the second element 2 allows two portions 22a, 22b of the second element 2 to be conserved that are situated on the same face of the said second element 2 and which extend from an interface region between the first element 1 and the second element 2 in opposite directions on either side of the said first element 1. Accordingly, each connection terminal 6a, 6b comprises an electrical contact region with an associated connection pad 21a, 21b which is not therefore accessible and an accessible area on a corresponding portion 22a, 22b intended to provide a contact formation for powering the resistive element 4 from the outside of the cavity 3.

It will then be understood that the first and second cases differ in the fact that they present the connection terminals 6a, 6b on two opposing faces (back and front faces) of the electronic component. The case will therefore be able to be chosen between the first case and the second case depending on the integration constraints of the electronic component.

The invention naturally also relates to a method for fabricating a plurality of electronic components such as described. This method notably provides the formation of the cavities in the electronic components at low temperature for the aforementioned reasons.

In this respect, as illustrated in FIGS. 4 to 13, the method for fabricating the plurality of electronic components such as described comprises a step for supplying (FIGS. 4 and 8) a first plate 25 comprising a base 26, preferably made of silicon (or plate or wafer made of silicon), on (in other words notably within) which a plurality of first hollows 23 is formed. The base 26 may therefore comprise the first hollows 23. The hollows 23 from the plurality of first hollows are therefore formed in the plate 25, notably within the base 26 of the first plate 25. The base 26 is preferably made of a material transparent to infrared. For this purpose, the base 26 is preferably made of silicon, notably single-crystal or polycrystalline, since it is thus transparent to infrared, however another material also transparent to infrared such as previously given may also be used. The said first plate 25 comprises suspended resistive elements 4 comprising metal, and each first hollow 23 is associated with at least one of the suspended resistive elements 4 and disposed facing the bottom 27 of the said first hollow 23. This bottom 27 of the first hollow is notably bounded by a surface of the base 26. As a consequence it is therefore necessary to close the first hollow 23 in order to form the desired cavities 3 for each of the electronic components. For this purpose, the method comprises a step for supplying a second plate 28 (FIGS. 4 and 8) comprising second hollows 24 intended to cooperate with the said first hollow 23 for the purpose of forming the enclosed cavities of the electronic components. This second plate 28 is preferably formed, entirely or in part, of silicon (notably single-crystal or polycrystalline), since it is thus transparent to infrared, however another material also transparent to infrared such as described hereinbefore may also be used. The second plate 28 may also be a wafer. Subsequently, the method comprises a step (FIGS. 5 and 9) for assembling the first and second plates 25, 28 comprising a step for eutectic soldering implemented within a chamber 29 under vacuum resulting in:

the formation of the enclosed cavities 3, under vacuum and leak tight, the localization of connection terminals 6a, 6b of the resistive elements 4 in hollow spaces 30 (notably also enclosed) bounded by the first and second plates 25, 28 and formed outside of the enclosed cavities 3. It will then be understood that the connection terminals 6a, 6b may be formed on one of the first or second plates 25, 28 prior to the assembly step.

From what has been said hereinabove, it will be understood that the electronic components may be formed using only two plates, notably using two wafers for example made of silicon. On a first wafer, the resistive elements and the first hollows 23 are formed and, on the second wafer, the second hollows 24 are formed. The term 'wafer' in the present description is understood to mean a semiconductor plate. The use of two plates for fabricating the plurality of electronic components allows, in the end, a controlled vacuum to be maintained within the cavities by virtue of the use of a 20 single eutectic soldering per cavity, in contrast to a multiplicity of eutectic soldering—also referred to as junctions—which would have the consequence of making the control of the leak-tight sealing of the enclosed cavities 3 more difficult.

The first and second hollows 23, 24, targeted within the framework of the method, are the same as those previously described. Notably, each first hollow 23 comprises an opening and a bottom connected by a sidewall of the said first hollow 23, the sidewall and the bottom of the first hollow 23 being bounded by a continuous surface of the same material, such as for example that of the base 26. Furthermore, each second hollow 24 comprises an opening and a bottom connected by a sidewall of the said second hollow 24, the sidewall and the bottom of the second hollow 24 being bounded by a continuous surface of the same material, such as for example that of the second plate 28.

Figure 6:
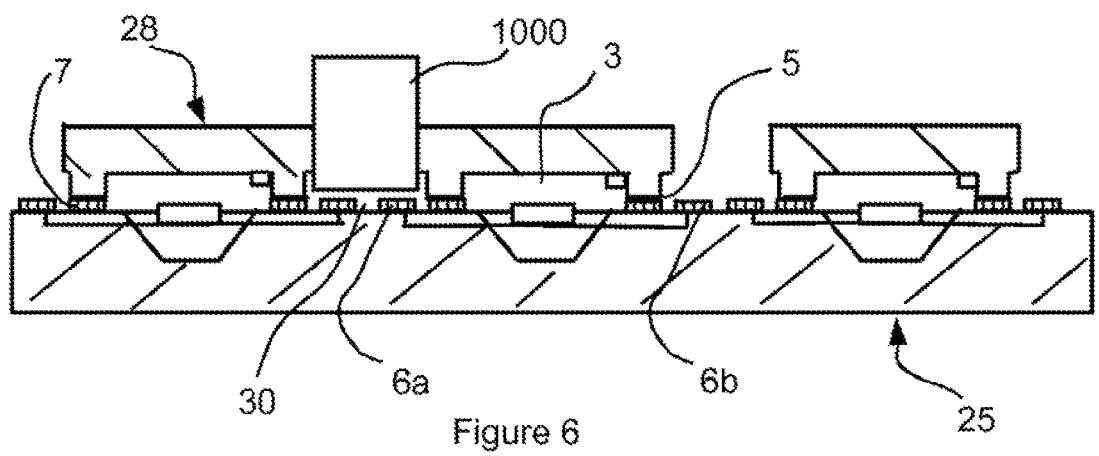
Figure 10:
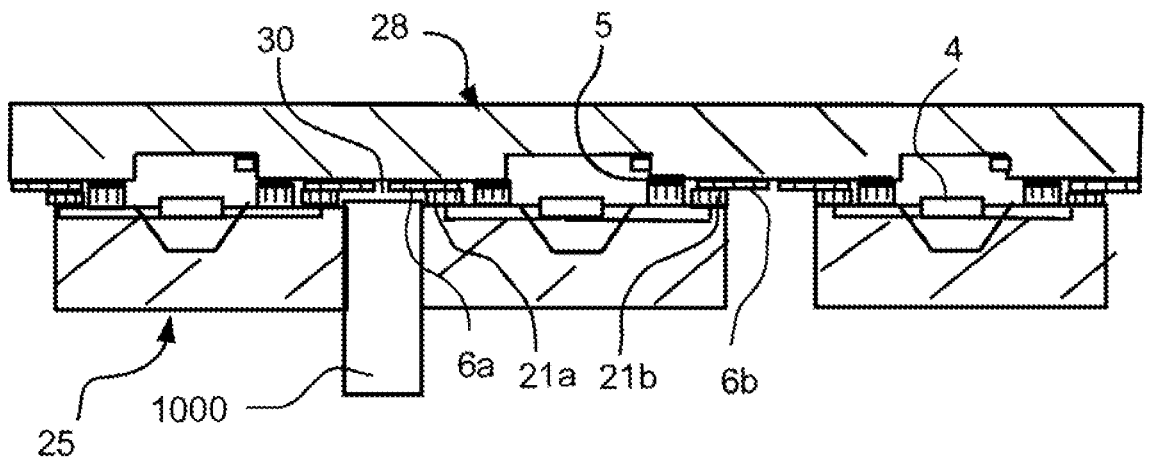

Subsequently, the method comprises (FIGS. 6 and 10) a step for removal of material in the hollow spaces 30 in order to make the connection terminals 6a, 6b accessible. FIGS. 6 and 10 show a blade 1000 to perform the sawing allowing the removal of material in order to liberate the connection terminals 6a, 6b. The removal of material in the hollow spaces 30 may for example be effected by removing, from each hollow space, a part of the assembly of the first and second plates which participates in bounding said hollow space 30.

Figure 7:
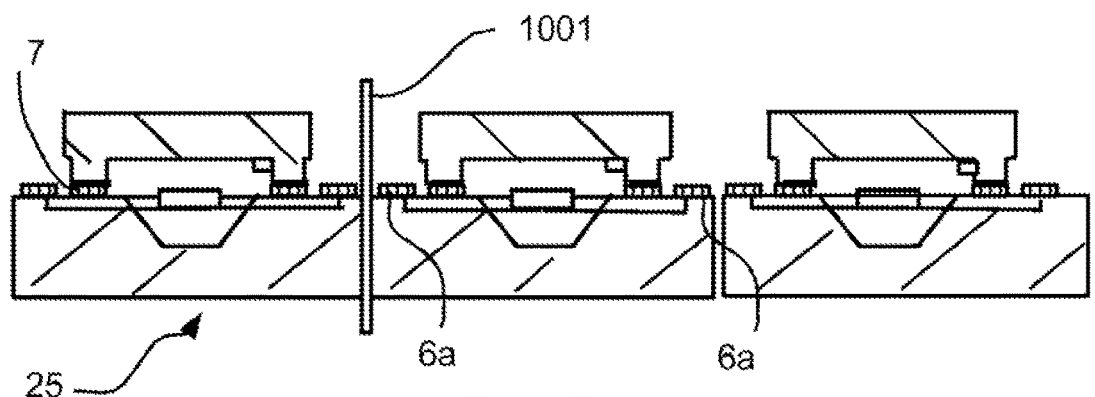
Figure 11:
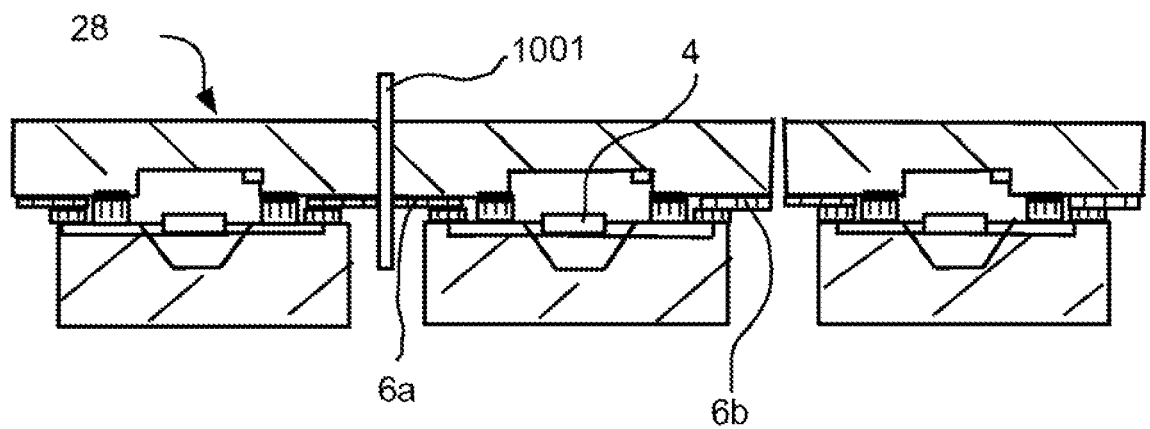

Depending on the applications, it is possible to make the components individual or to divide them into groups forming a single entity. For this purpose, the method may, where relevant, comprise a step for separation of the electronic components by removal of material (FIGS. 7 and 11).

Such steps are advantageous in that they enable the formation of the enclosed cavities 3 while limiting the increase in temperature of the whole assembly of the future electronic components and at the same time allowing all of the cavities of the various components to be formed simultaneously based on the same soldering step. As a consequence of this, such a method furthermore allows the fabrication of the electronic components according to a throughput adapted to large-scale production and, at the same time, allows the production costs to be reduced.

From what has been said hereinabove, it will be understood that the assembly step may furthermore comprise (FIGS. 5 and 9) the following steps: a step for placing the first and second plates 25, 28 in the chamber 29, a step for alignment of the first and second plates 25, 28, notably so that each first hollow can cooperate with a corresponding second hollow for the purpose of forming the corresponding enclosed cavity, a step for putting the chamber 29 under vacuum (notably to a pressure less than or equal to that indicated previously and corresponding to that inside of the cavities 3) comprising the first and second aligned plates 25, 28. Once the chamber 29 is under vacuum, the eutectic soldering step may be implemented by thermo-compression, in particular by individually heating each of the first and second plates 25, 28 when they are brought together. The individual heating of the first and second plates 25, 28 notably allows the deterioration of the resistive element owing to a difference in temperature between the two plates to be avoided. The individual heating may for example be implemented by using two heating elements 31, 32 respectively disposed in contact with the first plate 25 and the second plate 28.

The eutectic soldering step may be implemented by subjecting the assembly formed by the first and second plates 25, 28 to a temperature comprised between 350° C. and 400° C., and notably equal to 350° C.

Figure 4:
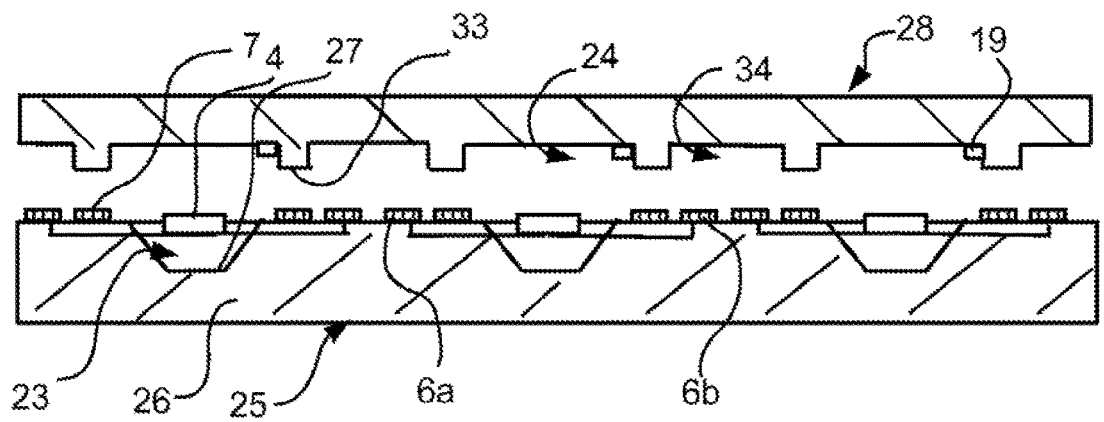
FIGS. 4 to 7 illustrate various steps of a method enabling the fabrication of a plurality of electronic components of the type in FIG. 1, FIGS. 8 to 11 illustrate various steps of a method allowing the fabrication of a plurality of electronic components of the type in FIG. 2, FIGS. 12 and 13 illustrate, on the other hand, two variants of a step respectively of the two aforementioned methods.
Figure 5:
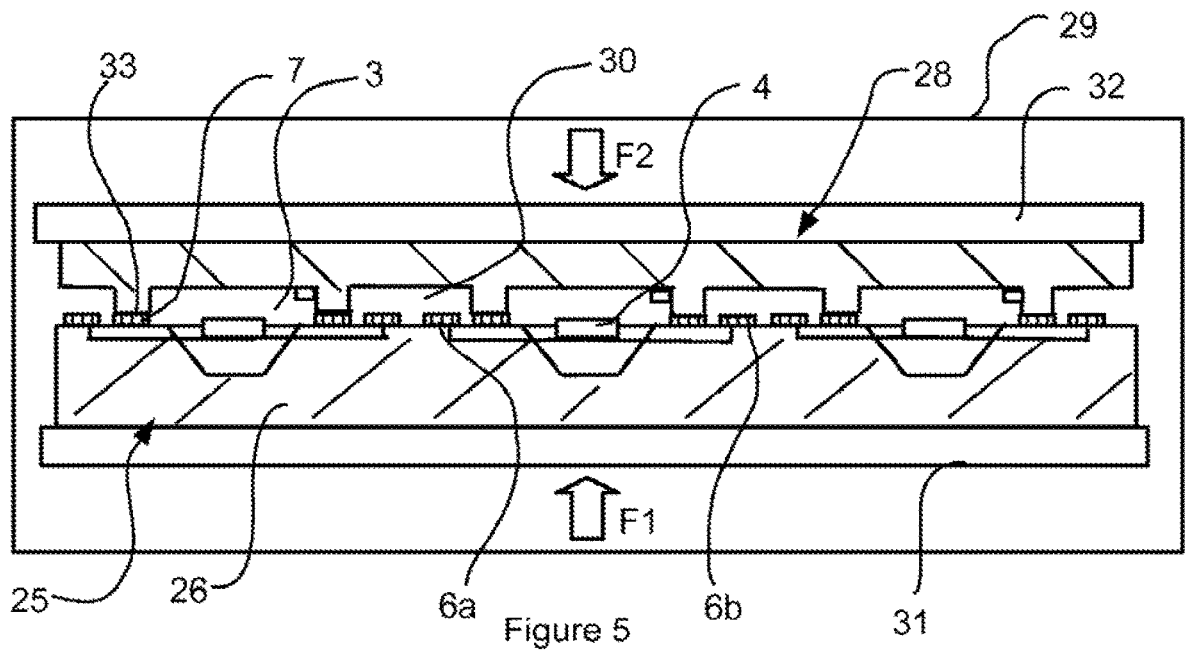
Figure 8:
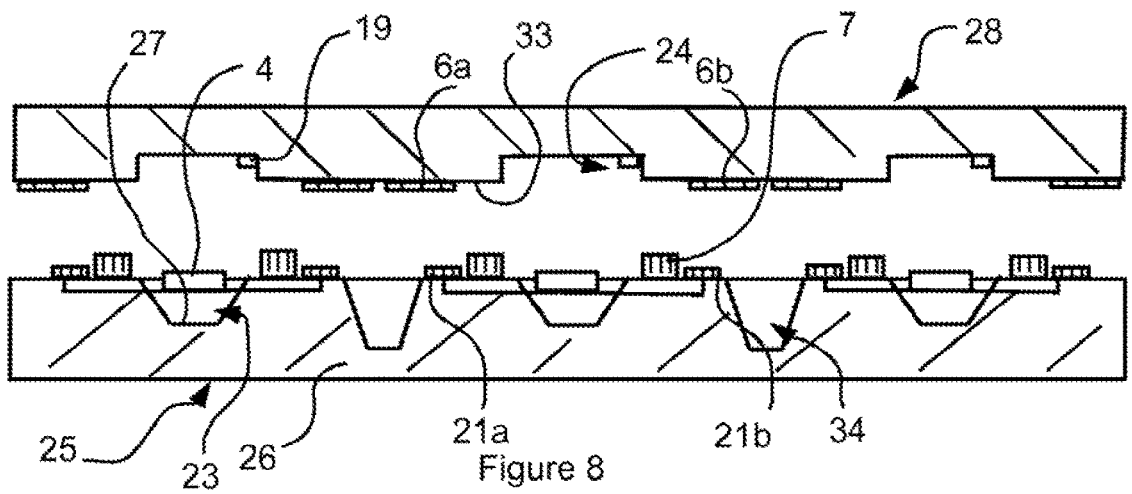
Figure 9:
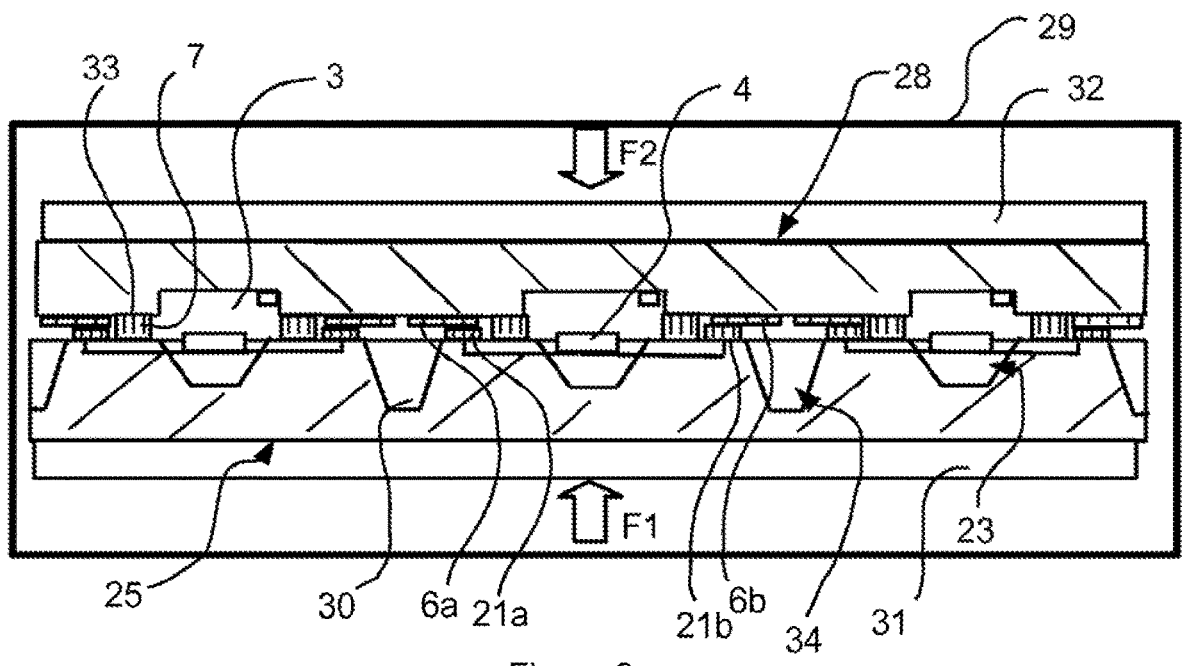

The eutectic soldering step uses, in particular, gold and silicon brought into contact, however other materials such as those listed previously (Au and In, or Cu and Sn, or Au and Sn, or Au and Ge, or Al and Ge) brought into contact may be used to carry out the soldering step which results in the formation of a eutectic alloy. In the Silicon/Gold case, the silicon preferably comes from the second plate 28 and the gold 35 from the first plate 25. According to one particular exemplary embodiment, the fabrication method comprises (FIGS. 4 and 8), prior to the assembly step and for each first hollow 23, a step for formation of the closed track 7 made of a first material (notably gold) arranged at the periphery of the said first hollow 23. This track 7 has a thickness comprised between 0.1 µm and 1 µm and notably equal to 0.2 µm, and a width comprised between 100 µm and 300 µm and notably equal to 160 µm. This track 7 must be sufficiently wide to adsorb a potential error in alignment of the first and second plates, i.e. more or less about 0.1 degrees to 0.2 degrees over 200 mm being about 100 µm. Furthermore, the second plate 28 comprises bearing faces 33 (FIGS. 4 and 8) made of a second material (notably silicon) each disposed in contact against the corresponding track 7 during the assembly step (FIGS. 5 and 9). Notably, each track 7 will be brought into contact with an associated bearing face 33 of the second plate 28. The first and second materials are notably chosen so as to form one of the following material pairs: gold and silicon, or Cu and Sn, or Au and Sn, or Au and Ge, or Al and Ge, or Au and In. Depending on the embodiment, those skilled in the art will be able to adapt the presence of the first and second materials on the first and second plates 25, 28, for example by depositing, if necessary, complementary tracks on the second plate 28 so as to form the bearing face 33. The eutectic soldering step then comprises a step for pushing (arrows F1 and F2 in FIGS. 5 and 9) the first and second plates 25, 28 towards each other while applying a temperature suitable for forming the eutectic soldering 5 (FIGS. 6 and 10) from the first and second materials. The tracks 7, in particular when they are made of gold, notably rest on a layer of $Si_3N_4$ as previously mentioned; this layer of $Si_3N_4$ forms a barrier against the diffusion of the material of the track 7 towards other layers of the first element 1. Subsequent to the assembly step, the tracks 7, notably made of gold, have a thickness that is reduced owing to the eutectic soldering which has formed an alloy, notably SiAu, all along the said tracks 7 (FIGS. 6 and 10).

The liberation of the connection terminals 6a, 6b (FIGS. 6 and 10) allows these connection terminals 6a, 6b to be connected to an electrical power supply source in order to activate the associated resistive element 4, in other words to raise its temperature to a desired operating temperature for the emission of a desired infrared radiation outside of the associated cavity 3. This liberation will of course preferably be implemented outside of the chamber 29 in which the soldering has been implemented.

The liberation of the connection terminals 6a, 6b (hence the step for removal of material) may be implemented in various ways, for example by using sawing, etching or polishing techniques. By sawing, it is possible to remove material from the assembly formed during the assembly step using a blade. By reactive dry etching (D-RIE for "Deep Reactive Ion Etching"), it is possible to remove material from the assembly formed during the assembly step, but in this case the connection terminals 6a, 6b will have been, prior to the assembly step, covered with a layer of oxide (not shown) in order to protect them, in particular when the latter comprise gold. By polishing, the planarization technique of chemical-mechanical polishing, also known in the field by the acronym CMP, could be used.

Figure 12:
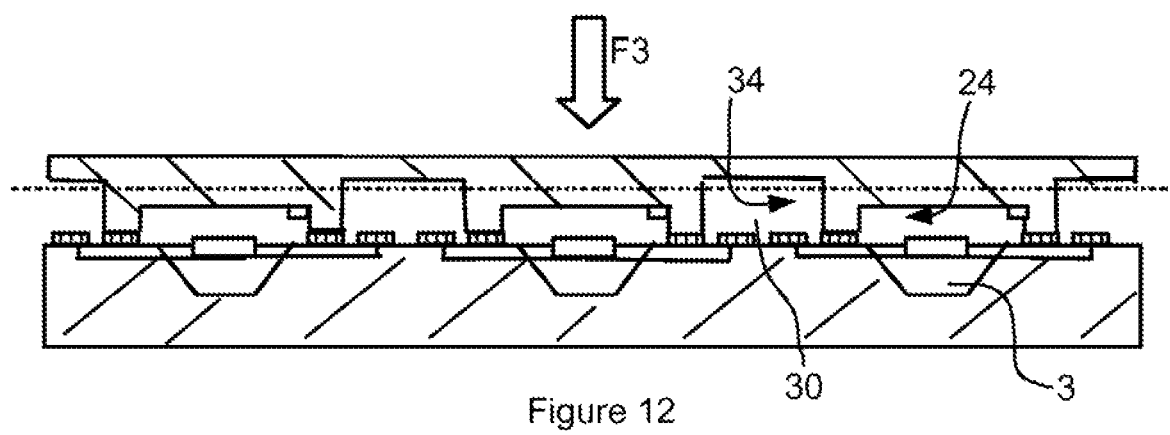

First and second cases for the positioning of the connection terminals 6a, 6b have been described hereinbefore. FIGS. 4 to 7 are notably associated with the first case, and FIGS. 8 to 11 are notably associated with the second case. This will of course have an influence with regard to the steps for supplying the first and second plates 25, 28 in the sense that these connection terminals 6a, 6b will be carried, notably prior to the assembly step, either by the first plate 25 (FIGS. 4 to 7) or by the second plate 28 (FIGS. 8 to 10). These connection terminals will preferably be made of gold or aluminium In FIGS. 4 to 7, it is the first plate 25 which comprises the connection terminals 6a, 6b of the resistive elements 4, and the step for removal of material in order to liberate the said connection terminals 6a, 6b (FIG. 6) is implemented by removal of material belonging to the second plate 28. In order to facilitate such an implementation, the second plate 28 comprises third hollows 34 (FIG. 4) each intended to form a hollow space 30 (FIG. 5) associated with a part of the first plate 25 where at least one of the connection terminals 6a, 6b is located. The third hollows 34 are (except if they are situated on the periphery of the second plate 28) each disposed between a corresponding pair of two adjacent second hollows 24 (FIG. 4). The step for removal of material therefore takes place, for each hollow space 30, at a wall of the said hollow space 30 situated between two adjacent enclosed cavities 3 (FIG. 6). It will be noted that, in the example in FIG. 12, where a polishing is carried out according to the arrow F3, the depth of the third hollows 34 must be greater than those of the second hollows 24 in the sense that the polishing must allow the opening of the hollow spaces 30 in order to make the connection terminals 6a, 6b accessible but without prejudice to the closing of the cavities 3 of the various electronic components: more particularly, the dashed line in FIG. 12 illustrates the place where the polishing must be stopped. According to the embodiment in FIGS. 4 to 7 and as is more particularly illustrated in FIG. 7, the separation step comprises the removal of material belonging to the first plate 25, notably by sawing for example by means of a blade 1001.

Figure 13:
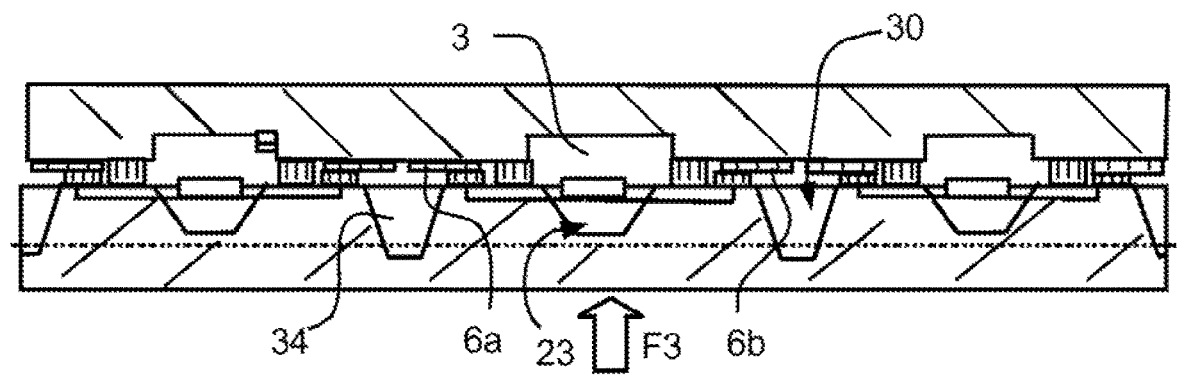
Figure 14:
FIGS. 14 to 21 illustrate one way of forming a suspended resistive element of the type used in the present invention; according to FIGS. 14 to 19, these show a cross section not including the suspension arms.
Figure 15:
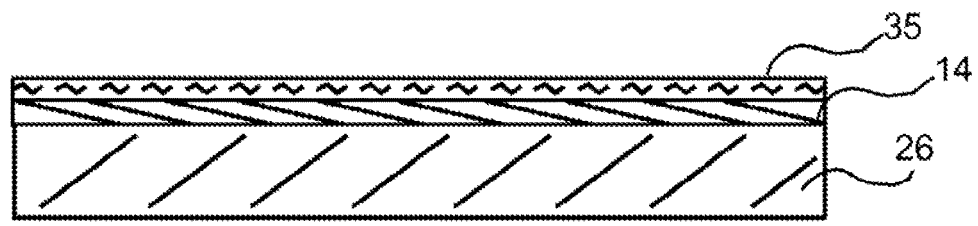
Figure 16:
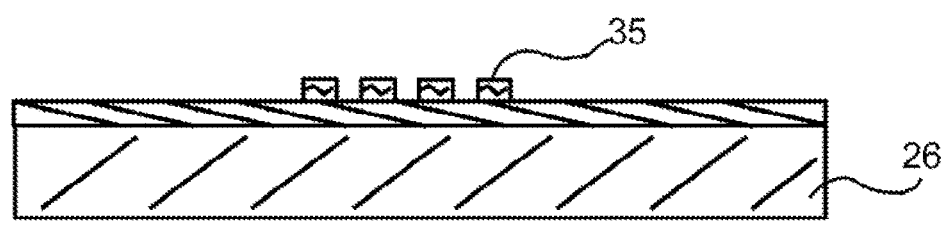
Figure 17:
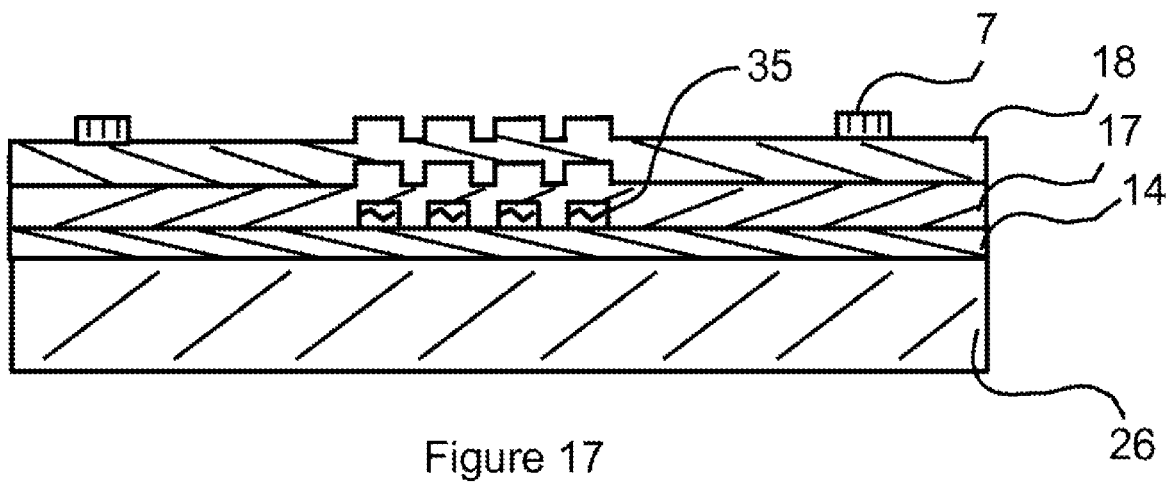
Figure 18:
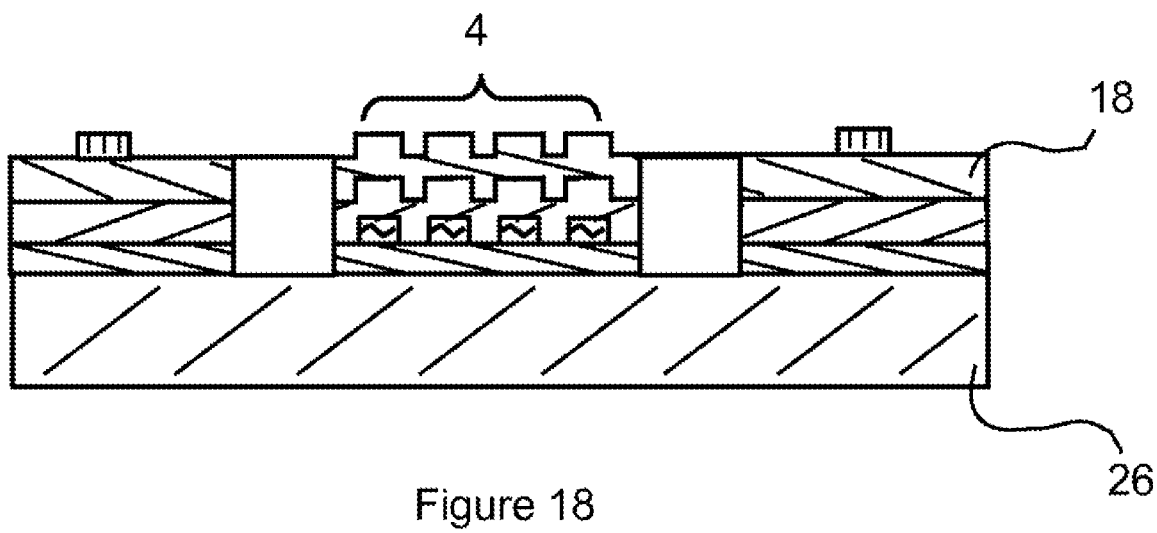
Figure 19:
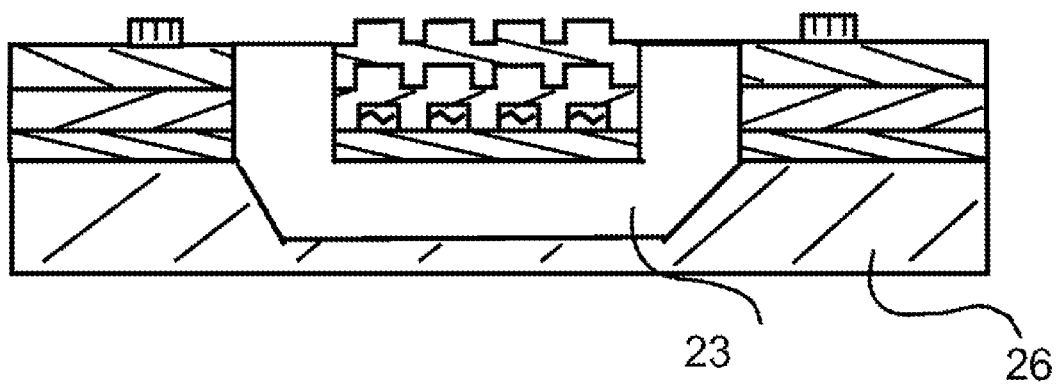
Figure 20:
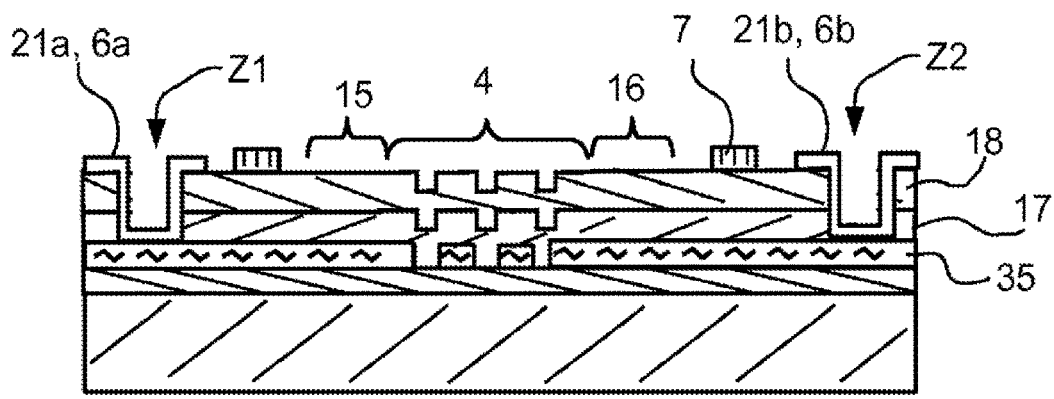
Figure 21:
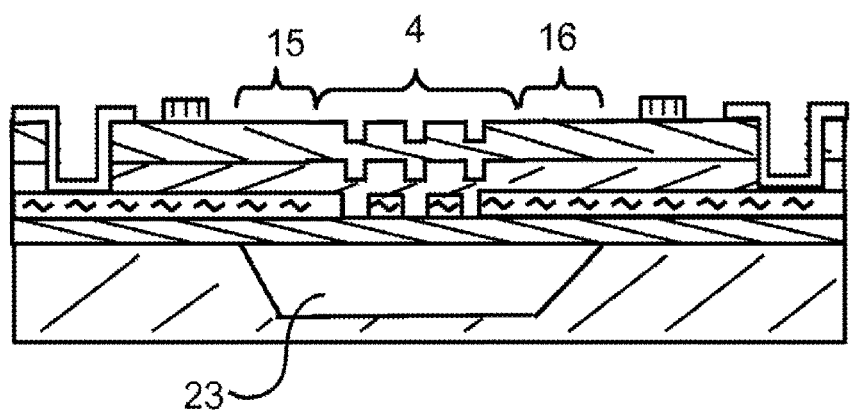

FIGS. 8 to 11 illustrate the second case where the connection terminals 6a, 6b are carried by the second plate 28 (notably prior to the implementation of the assembly step), the first plate 25 comprises connection pads 21a, 21b (notably made of gold or aluminium and carried by the first plate prior to the implementation of the assembly step) each electrically connected to at least one resistive element 4, and third hollows 34 (FIGS. 8 and 9) intended to form the hollow spaces 30. The third hollows 34 are each intended to former a hollow space 30 associated with a part of the second plate 28 where at least one of the connection terminals 6a, 6b is located. The third hollows 34 are (except if they are disposed at the periphery of the first plate 25) each disposed between a corresponding pair of two adjacent first hollows 23. Furthermore, the associated assembly step results in an electrical contact being made between the connection pads 21a, 21b and the corresponding connection terminals 6a, 6b (FIG. 9) and the formation of the hollow spaces 30 comprising the connection terminals 6a, 6b. Generally, the assembly step allows a bonding to be formed between the connection pads and the connection terminals. In order to liberate the connection terminals 6a, 6b, the step for removal of material may be implemented by removal of material belonging to the first plate 25 (FIG. 10), for example by using a blade 1000 on the hollow spaces 30. It will be noted that, in the example using polishing illustrated in FIG. 13, the depth of the third hollows 34 must be greater than that of the first hollows 23 in the sense that the polishing must allow the opening of the hollow spaces 30 in order to make the connection terminals 6a, 6b accessible but without prejudice to the closing of the cavities 3 for the various electronic components: more particularly, the dashed line in FIG. 13 illustrates the place where the polishing according to the arrow F3 must be stopped. According to the embodiment in FIGS. 8 to 11 and as is more particularly illustrated in FIG. 11, the separation step comprises the removal of material belonging to the second plate 28, notably by sawing for example by means of a blade 1001.

Generally, when the step for removal of material in order to liberate the connection terminals 6a, 6b and the step for separation of the electronic components are implemented by sawing, the step for removal of material comprises the use of a first blade 1000 (FIGS. 6 and 10) having a first width of blade and the step for separation of the electronic components comprises the use of a second blade 1001 (FIGS. 7 and 11) having a second width less than the first width.

During the method, the future electronic components are notably spaced out in such a manner that the hollow spaces 30 situated between two adjacent enclosed cavities 3 each comprise connection terminals for two different electronic components. As a consequence, it is thus possible to maximize the number of components per plate.

In the embodiment where a gas trap 19 is placed within the cavities, the latter may be formed in the first and/or the second hollow (FIGS. 4 and 8) prior to the assembly step, and notably the soldering step concomitantly allows the activation of the gas trap 19 so that the latter is allowed to participate to vacuum the cavities 3.

From all that has been previously said, it will be understood that the first plate may be obtained by forming, from the silicon base, a plurality of sources for example such as described in the document "Sensors and Actuators A: Physical" in the article entitled "Mid-IR source based on a free-standing microhotplate for autonomous $CO_2$ sensing in indoor applications" by P. Barritault et al. published in "Sensors and Actuators A 172 (2011) 379-385" prior to forming the gold tracks then to placing and soldering the second plate to the first plate. By way of example, a step for formation of the first plate may comprise the following steps, illustrated in FIGS. 14 to 21:

provide a plate/base preferably made of silicon 26 (FIG. 14), deposit a first layer 14 (FIG. 15) for relaxation of the stresses on the silicon plate 26, notably of $Si_3N_4$ (for example by LPCVD deposition for "Low-Pressure Chemical Vapour Deposition"), form a stack 35 of layers on the first relaxation layer 14 comprising a metal layer disposed between two barrier layers against the diffusion of the metal layer, this stack is notably formed by the following successive layers TiN/Pt/TiN (for example the stack is formed by PVD deposition for "Physical Vapour Deposition"), structure (FIG. 16), for example by ion or reactive etching, said stack 35 of layers so as to form, within each future electronic component, a part of the said at least one associated resistive element 4 and a part of the future suspension arms of the said at least one associated resistive element which then extend as far as contact formation areas where, depending on the case, the aforementioned pads or connection terminals could be formed, in particular, the electrically conducting parts of the arms are such that they are less electrically resistive than the resistive element 4, deposit (FIG. 17) a passivation layer 17, notably of $SiO_2$ (for example by PECVD for "Plasma-Enhanced Chemical Vapour Deposition") on the structured stack 35, deposit (FIG. 17) a second layer 18 for relaxation of the stresses, notably of $Si_3N_4$ (for example by LPCVD) on the passivation layer 17, etch (FIG. 20), for example by reactive etching (RIE for "Reactive-Ion Etching") the second layer 18 for relaxation of the stresses and the passivation layer 17 in the contact formation areas Z1, Z2 in order to liberate the electrical access to the stack 35, form the tracks 7, in particular of gold, notably using a deposition by evaporation (FIGS. 17 and 20) and the pads, or where relevant the connection terminals, 21a, 21b, 6a, 6b. The pads or connection terminals may be formed from the titanium nitride of the stack 35 followed by a gold deposition. It will be noted that, in order to accelerate the method, the gold track 7 and at least a gold part of the pads or of the connection terminals will be formed from a common gold deposition. The deposition, notably of gold, will be done preferably by evaporation in order to limit the quantity of gas trapped during the deposition, etch the assembly (FIG. 18), preferably by reactive etching (RIE), starting from the second layer 18 for relaxation of the stresses down to the silicon plate 26 in such a manner as to define the resistive elements 4 (FIG. 18) together with the associated suspension arms parts 15, 16 (FIG. 20) intended to be disposed within the future enclosed cavities, etch (FIGS. 19 and 21) the silicon base/plate 26, for example by anisotropic chemical etching (notably according to the TMAH (for "Tetramethylammonium Hydroxide") or KOH (for "Potassium Hydroxyde") techniques, with a preference for TMAH owing to its good compatibility with microelectronics), which results in the formation of the first hollow 23 and the suspension of the resistive elements 4, notably via their arms 15, 16, above the first hollows 23.

Generalizing, the method may comprise, prior to supplying the first plate 25, a step for formation of the first plate 25, this step for formation of the first plate comprising:

a step for supplying a base 26 taking the form of a plate, for example a silicon plate or wafer, a step for formation of the resistive elements 4 on this base 26, notably on one face of this base, the said resistive elements being intended to form sources of infrared radiation, a step for etching the base 26 on the side of the face of the base 26 where the resistive elements 4 are formed so as to form the first hollow 23 in the base 26. In other words, the etching step allows the resistive elements to be suspended after their formation.

The result of the preceding steps is that each gold track 7 rests on a layer of $Si_3N_4$. FIGS. 14 to 21 shows the fabrication of a part of a single component, however these steps carried out on the entire silicon plate 26 using microelectronics techniques can allow the concomitant formation of a plurality of first hollows each associated with at least one suspended resistive element. With regard to the thicknesses of the various layers used, they correspond to those previously described in the framework of the electronic component. As far as the second plate is concerned, it may be obtained starting from a silicon plate structured in a suitable manner so as to form the second hollows 24 and, where relevant, the third hollows 34. This structuring may be implemented for example by chemical or reactive etching.

The present invention allows an infrared source with metal resistor emitter to be encapsulated while at the same time allowing the connection terminals to be readily positioned without limitation on the back or front face. The method described is:

compatible with the use of metal layers, capable of guaranteeing a leak-tight sealing and capable of guaranteeing the under vacuum condition for a long period, capable of transferring the power supply connections for the resistor outside of the volume under vacuum, capable of providing connection terminals for the resistive element either on the front face or on the back face of the electronic component.

Furthermore, the method allows an assembly of resistive elements with metal layer formed on a common silicon plate to be protected in a leak-tight and collective manner, and under vacuum, while at the same time allowing an individual dicing of the electronic components.

Such an invention with the placing under vacuum of the resistive element 4 results in the electrical power consumption of the electronic component being reduced by a factor of 10 with respect to the same electronic component but whose resistive element were not placed under vacuum.

The invention also relates to a use of an electronic component such as described as a source of infrared radiation for the gas detection.

Figure 22:
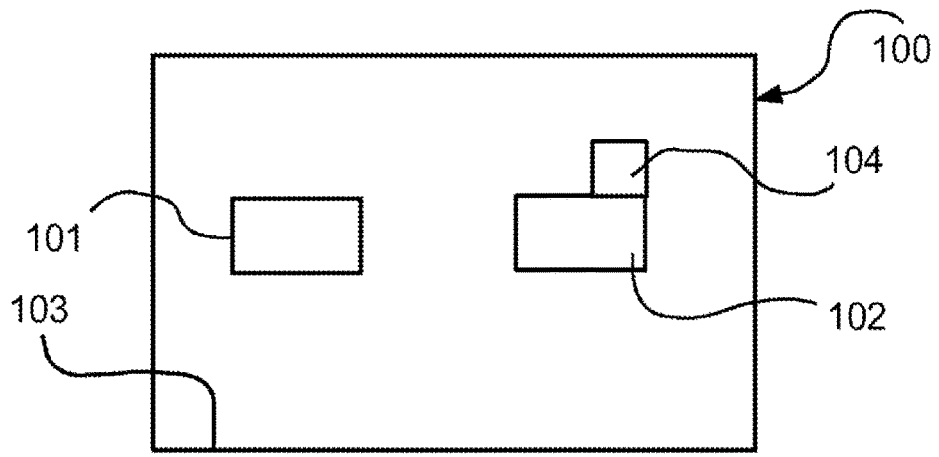
FIG. 22 illustrates schematically a gas detector comprising an electronic component according to the invention.

It goes without saying that the invention also relates to a gas detector 100 (FIG. 22) comprising an electronic component 101 such as described and a measurement sensor 102 capable of measuring infrared radiation coming from the electronic component 101. In particular, the gas detector 100 comprises an optical cavity 103 in which the electronic component 101 and the sensor 102 are placed. The gas detector may comprise an analysis module 104 connected to the sensor 102 and capable of determining the presence of a gas from a measurement of the intensity of the radiation captured. Notably, the gases able to be detected by the gas detector are HF, HCl, $SO_2$, $SO_3$, $CO_2$, HBr, $H_2S$, $C_2H_6$, $C_3H_8$, $C_4H_{10}$, NO, $COCL_2$, $BF_3$, $NO_2$, $CH_4$, $HNO_3$, a volatile organic compound for example $CH_3COCH_3$, $B_2H_6$, CO, $CS_2$, HCN, $WF_6$, $N_2O$, $NH_3$, $AsH_3$, a polycyclic aromatic hydrocarbon, benzene, toluene, three isomers of xylene, $C_2H_4O$, $BCl_3$.

One common application of gas detectors is in the dynamic management of air conditioning systems and in the prevention of domestic accidents associated with malfunctions of the gas/fuel/wood means of heating (risks of explosion following gas leaks, blocking of chimneys, and production of excesses of CO, etc.). Although the concentration of $CO_2$ is a good indicator of the occupation fraction and renewal rate of the air, CO is extremely toxic. On the other hand, butane, propane and methane, generally used as domestic gases, are explosive when their concentration exceeds a few % (~2% for butane and propane, ~5% for methane). There is therefore a real need for the use gas detectors.

Gases have well-defined spectral signatures in the infrared (vibrations of the molecules), thus making possible the detection over absorption spectral bands of characteristics of the gas sought for example using the absorption spectral band about 4.25 µm of $CO_2$ for detecting it.

The electronic component may potentially incorporate a filtering and/or antireflection element. The filtering element allows the spectral band to be selected that is characteristic of the compound that it is sought to detect, for example, for $CO_2$, 4.25 µm plus or minus 100 nm will be taken. With regard to the antireflection element, it allows the optical index of the materials used in the framework of the detector to be adapted, the antireflection element may for example comprise one or more layers (e.g. $SiO_2$, $Si_3N_4$) having variable thicknesses as a function of the wavelength and comprised between a few tens of nm and a few hundreds of nm.

The invention claimed is:

1. An electronic component for generating infrared radiation, comprising:
   a first element and a second element arranged in such a manner as to form an enclosed cavity under vacuum within which at least one resistive element of the electronic component is suspended, wherein
   said at least one resistive element comprising metal and configured to generate the infrared radiation,
   the first and second elements being joined by eutectic soldering to seal the enclosed cavity in a leak-tight manner,
   said electronic component comprising connection terminals situated outside of the enclosed cavity and electrically connected to the suspended resistive element,
   the enclosed cavity has an internal pressure of less than $10^{-2}$ mbar, and
   the at least one resistive element is suspended by suspension arms belonging to the first element.

2. The electronic component according to claim 1, wherein the eutectic soldering is formed with silicon and gold, or Au and In, or Cu and Sn, or Au and Sn, or Au and Ge, or Al and Ge.

3. The electronic component according to claim 1, wherein a residual gas trap is situated within the enclosed cavity.

4. The electronic component according to claim 1, wherein the first element comprises the connection terminals.

5. The electronic component according to claim 1, wherein the second element comprises the connection terminals, the first element comprises connection pads electrically connected to the at least one resistive element, the connection terminals each being in electrical contact with at least one of the connection pads.

6. The electronic component according to Claim 1, wherein the at least one resistive element comprises at least one structured part of a stack comprising successive layers as follows: a first barrier layer to prevent diffusion of a metal layer, the metal layer of platinum, a second barrier layer to prevent diffusion of the metal layer, wherein the first and second barrier layers are of titanium nitride.

7. The electronic component according to claim 6, wherein said stack forms a part of the suspension arms suspending the at least one resistive element and extends in a direction of the connection terminals.

8. The electronic component according to claim 1, wherein the enclosed cavity is provided by a single ribbon of eutectic soldering.

9. The electronic component according to claim 1, wherein the enclosed cavity is bounded, at least in part, by a hollow formed in the first element, said hollow comprising a bottom oriented towards the at least one resistive element, said hollow being hounded by a continuous surface of same material.

10. A gas detector comprising the electronic component according to claim 1 and a sensor configured to measure the infrared radiation coming from the electronic component.

11. A method of fabrication of electronic components, the method comprising:
   supplying a first plate comprising a base, on which plurality of first hollows is formed, the first plate comprising suspended resistive elements comprising metal, and each first hollow is associated with at least one of the suspended resistive elements disposed facing a bottom of the respective first hollow, the bottom being bounded by a surface of the base,
   supplying a second plate, comprising second hollows configured to cooperate with the first hollows and form enclosed cavities of the electronic components,
   assembling the first and second plates comprising eutectic soldering implemented within a chamber under vacuum which results in:
      formation of the enclosed cavities, under vacuum and leak tight,
      localization of connection terminals of the suspended resistive elements in hollow spaces bounded by the first and second plates and formed outside of the enclosed cavities,
   removal of material n the hollow spaces in order to make the connection terminals accessible.

12. The method according to claim 11, wherein the eutectic soldering uses gold and silicon, or Cu and Sn, or Au and Sn, or Au and Ge, or Al and Ge, or Au and In, brought into contact.

13. The method according to claim 11, further comprising, prior to the assembling, for each first hollow, formation of a closed track made of a first material arranged at a periphery of the respective first hollow, wherein the second plate comprises bearing faces made of a second material, each bearing face disposed in contact against a corresponding track during the assembling, the eutectic soldering comprising pushing the first and second plates towards each other while applying a suitable temperature in order to form the eutectic soldering from the first and second materials.

14. The method according to claim 11, wherein the first plate comprises the connection terminals, and wherein the removal of material is implemented by removal of material belonging to the second plate, and wherein the removal of material is implemented by a technique chosen from amongst: sawing, polishing, and etching.

15. The method according to claim 11, wherein
   the connection terminals are carried by the second plate,
   the first plate comprises connection pads each electrically connected to at least one of the suspended resistive elements, and third hollows to form the hollow spaces,
   the result of the assembling is an electrical contact being made between the connection pads and corresponding connection terminals and formation of the hollow spaces comprising the connection terminals.

16. The method according to claim 15, wherein the removal of material is implemented by removal of material belonging to the first plate in the hollow spaces.

* * * * *